(12) United States Patent
Niederbacher

(10) Patent No.: US 12,234,437 B2
(45) Date of Patent: Feb. 25, 2025

(54) BIOGAS PLANT FERMENTER TANK, SERVICE DEVICE FOR MOUNTING ON A BIOGAS PLANT FERMENTER TANK AND METHOD FOR OPERATING A BIOGAS PLANT FERMENTER TANK

(71) Applicant: Michael Niederbacher, Bruneck (IT)

(72) Inventor: Michael Niederbacher, Bruneck (IT)

(\*) Notice: Subject to any disclaimer, the term of this patent is extended or adjusted under 35 U.S.C. 154(b) by 745 days.

(21) Appl. No.: 15/733,450

(22) PCT Filed: Feb. 1, 2019

(86) PCT No.: PCT/EP2019/052510
§ 371 (c)(1),
(2) Date: Jul. 31, 2020

(87) PCT Pub. No.: WO2019/149891
PCT Pub. Date: Aug. 8, 2019

(65) Prior Publication Data
US 2021/0102149 A1    Apr. 8, 2021

(30) Foreign Application Priority Data

Feb. 2, 2018 (DE) .................. 10 2018 000 841.0
Feb. 6, 2018 (DE) .................. 10 2018 000 927.1

(51) Int. Cl.
*C12M 1/107* (2006.01)
*C12M 1/00* (2006.01)
*C12M 1/06* (2006.01)

(52) U.S. Cl.
CPC ............ *C12M 21/04* (2013.01); *C12M 23/38* (2013.01); *C12M 27/02* (2013.01); *C12M 29/06* (2013.01)

(58) Field of Classification Search
CPC ...... C12M 21/04; C12M 23/38; C12M 27/02; C12M 29/06

USPC ...................................................... 435/289.1
See application file for complete search history.

(56) References Cited

U.S. PATENT DOCUMENTS

2015/0291924 A1\* 10/2015 Czwaluk ............... C12M 23/00
  366/343
2015/0315535 A1\* 11/2015 Kromus ................ C12M 29/18
  435/167

FOREIGN PATENT DOCUMENTS

EP        2497822 A1 \*  9/2012  .......... B01F 7/00741

OTHER PUBLICATIONS

EP2497822A1 Machine English Translation (Year: 2012).\*

\* cited by examiner

*Primary Examiner* — Michael L Hobbs
*Assistant Examiner* — Lenora A Abel
(74) *Attorney, Agent, or Firm* — Southeast IP Group, LLC; Thomas L. Moses

(57) ABSTRACT

The invention relates to a biogas plant fermenter tank (1) comprising a substantially liquid substrate (6) accommodated in the tank inner chamber (5) and at least one stirring device (8) arranged in the tank inner chamber (5). According to the invention, an injection device (9) having at least one delivery pump (10) which extracts the injection liquid (12), and at least one injection nozzle element (11) which is fluidically connected to the at least one delivery pump (10), is provided. The injection liquid (12) can be injected into the fermenter tank (1) by means of said injection device in such a way that the injection liquid impinges as a liquid jet (13) from above onto the surface of a floating layer (7) of the substrate (6) and wets the latter.

26 Claims, 7 Drawing Sheets

BIOGAS PLANT FERMENTER TANK, SERVICE DEVICE FOR MOUNTING ON A BIOGAS PLANT FERMENTER TANK AND METHOD FOR OPERATING A BIOGAS PLANT FERMENTER TANK

The invention relates to a biogas plant fermenter tank according to the preamble of claim 1, a service device for mounting on a tank wall of a biogas plant fermenter tank, and a method for operating a biogas plant fermenter tank. Furthermore, the invention relates to a biogas plant.

EP 2 497 822 A1 already discloses a biogas plant fermenter tank with a service device which has a service opening on the top side that can be closed gas-tightly by means of a covering device, through which opening a submersible agitator, which is height-adjustably guided on a guide mast, can be moved out of the fermenter tank and back into the fermenter tank in substantially gas-tight fashion for maintenance and service works. The service opening on the top side that can be closed gas-tightly by means of the covering device is part of a walkable platform which is arranged on the top side and to which a tank wall and a foil roof of the fermenter tank are connected.

A general problem with biogas plant fermenter tanks is that, depending on the type and consistency of the substrate introduced into the tank inner chamber, floating or cover layers can form which can impede the separation and/or extraction of biogas. Therefore, it is already known that these floating cover layers can be destroyed and removed completely and stirred into the substrate with relatively high energy expenditure by means of the stirring devices arranged in the tank inner chamber. A further disadvantage of this stirring of the floating layers by means of the stirring devices arranged in the tank inner chamber, apart from the relatively high energy consumption, is that the stirring devices must be led very far upwardly to the surface of the substrate, which can lead to a deterioration of the efficiency with regard to a desired complete through mixing of the substrate, especially in large-volume tanks with high filling heights.

Furthermore, it is known from DE 10 2008 038 262 B4, for example, to dispense completely with the use of stirring devices and to apply liquid substrate, taken from the bottom of the fermenter tank, to the substrate surface and thus to the floating and/or top layers via an injection nozzle. This is intended to keep the surface of the floating and/or top layer moist. However, this is accompanied by the disadvantage that the substrate is not completely mixed, and thus the fermenter tank content is not substantially homogenized, and therefore the fermentation processes take place in different vertical zones in the fermenter, which is undesirable.

On the other hand, the object of the present invention is to create a biogas plant fermenter tank or a method for operating a biogas plant fermenter tank by means of which a high biogas yield can be achieved with reduced energy expenditure despite the presence of floating layers. A further object of the invention is to provide a suitable service device for biogas plant fermenter tanks.

This object is achieved with the features of the independent claims. Advantageous embodiments are the subject of the dependent claims referring back to the independent claims.

According to claim 1, a biogas plant fermenter tank, in particular a biogas plant fermenter tank of a biogas plant having one or more fermenter tanks, is proposed and has a substantially liquid substrate accommodated in the tank inner chamber. Furthermore, the biogas plant fermenter tank has at least one stirring device arranged in the tank inner chamber. In accordance with the invention, an injection device is provided in addition to the at least one stirring device and has at least one delivery pump by means of which injection liquid can be drawn in or extracted, preferably from the substrate of the fermenter tank or from another fermenter tank of the biogas plant. Furthermore, the injection device has at least one injection nozzle element which is fluidically connected to the delivery pump and by means of which the injection liquid sucked in or extracted by means of the at least one delivery pump can be injected into the fermenter tank in such a way that, relative to a direction of the vertical axis of the fermenter tank, it impinges as a liquid jet from above onto the surface of a floating layer of the substrate and wets the latter. Furthermore, according to the invention, it is provided that the at least one stirring device, preferably a plurality of stirring devices spaced apart from one another (for example in the circumferential direction of the fermenter tank), is arranged in the tank inner chamber in such a way that, by means of this, the substrate in the region below the floating layer can be substantially completely homogenized and/or mixed without stirring the floating layer into the substrate.

With the solution according to the invention, a substantially complete homogenization or mixing of the substrate in the fermenter tank takes place on the one hand by means of the stirring devices, which is of particular advantage for the fermentation process in the substrate and thus for a high biogas yield. Since, with these stirring devices, which preferably have mechanical stirrers such as stirring blades or propellers, etc., and can be driven electrically, hydraulically or pneumatically, it is no longer necessary to stir in the floating layers, these stirring devices can be operated with a significantly lower energy expenditure than is the case if the floating layers additionally have to be broken up and stirred into the substrate.

The fact that in the solution according to the invention the floating layers are further exposed on their surface to a liquid jet, which is sucked in or extracted from the substrate of the fermenter tank or alternatively or additionally from another fermenter tank of an associated biogas plant, ensures that these floating layers participate in the fermentation process, even without being stirred into the substrate. Due to the fissured surface structure of the floating layer, the bacteria in the liquid jet also find a sufficient surface to attack for an effective fermentation process with high biogas yield. Even though the invention is generally always described hereinafter in conjunction with the sucking or extraction of the substrate from the same fermenter tank, i.e. from the fermenter tank on which the at least one injection nozzle element is arranged, because this is the preferred embodiment, it should be expressly pointed out again at this juncture that, in conjunction with a biogas plant which has a plurality of fermenter tanks, i.e. for example at least one pre-fermenter tank and/or at least one main fermenter tank and/or at least one post-fermenter tank, the injection liquid can be sucked in or extracted alternatively or additionally from one or more of these further fermenter tanks of a biogas plant, and this is expressly included within the scope of protection.

With the solution according to the invention, in which a conventional, preferably mechanical stirring is combined with an injection device, a homogenized or fully mixed substrate can thus be achieved in an advantageous manner in the region below the floating layers by means of the at least one stirring device, which results in a high biogas yield with a relatively low energy expenditure. Furthermore, by wetting the surface of the floating layers, an additional high biogas yield is achieved by incorporating these floating layers into the fermentation process.

As already described above, the at least one stirring device is preferably a mechanical stirring device with a stirring unit, a stirring propeller or the like. For substantially complete homogenization or mixing of the substrate, it is of particular advantage if a plurality of stirring devices are provided or arranged in the fermenter tank spaced apart from one another in the circumferential direction of the fermenter tank.

In addition, it should be noted that the term "nozzle" in the present context is to be interpreted broadly and includes any outlet opening or outlet opening geometry, i.e. in particular also outlet opening geometries which run in a straight line or widen, and not only outlet opening geometries which narrow in the conventional nozzle-like sense.

In addition, a particularly preferred embodiment is one in which the at least one stirring device is formed by an agitator, in particular by a submersible agitator and/or in particular with a stirring unit or propeller, which is guided in the tank inner chamber in a height-adjustable manner along an agitator guide mast arranged in the fermenter tank and oriented in the direction of the vertical axis of the tank. By means of such agitators, which are arranged in the tank inner chamber along an agitator guide mast arranged in the fermenter tank and height-adjustable in the direction of the vertical axis of the tank, a particularly advantageous mixing of the substance arranged in the fermenter tank is achieved. This is particularly the case also when, with large fermenter tanks with diameters of, for example, 10 to 50 m, a plurality of agitators are arranged in the tank inner chamber spaced apart from one another (for example in the circumferential direction of the fermenter tank) and guided height-adjustable on agitator guide masts, which are each oriented in the direction of the vertical axis of the tank.

A particularly preferred design provides for the at least one injection nozzle element to project into the tank inner chamber by means a front end having an injection nozzle, preferably gas-tightly, while a rear, connection-side end of the injection nozzle element lies or is arranged outside the tank inner chamber. This allows a particularly simple connection of the delivery pump (for example by means of a pressure line) to the injection nozzle element, with the connection being also easily accessible for servicing. Alternatively, however, the at least one injection nozzle element and thus also its connection-side end can also be arranged fully or completely in the tank inner chamber. This solution is particularly advantageous in conjunction with an internal delivery pump, since no lines, such as a pressure line of the delivery pump, have to be routed from outside the fermenter tank through walls into the tank inner chamber.

In accordance with a particularly preferred specific embodiment, the tank opening is provided with a roof to cover or overlay it. The roof is preferably formed by a foil roof, although a concrete ceiling as roof of the fermenter tank or the tank opening is also possible in principle. Furthermore, a service device is provided, which has a service platform arranged in the region of the roof and/or forming part of the roof, and can be walked on and is formed by a separate component, the service platform being, for example, a walkable and/or level platform plate, for example made of metal (for example made of steel, in particular stainless steel). This service platform is preferably connected by means of at least one connecting element, preferably detachably and gas-tightly, to a tank wall, in particular to a tank side wall, and has a roof connection region to which the roof is connected, preferably detachably and gas-tightly. Furthermore, this service device comprises the at least one injection device or at least one injection device. With such an embodiment according to the invention, the injection device thus forms an advantageous component of a service device having a service platform, so that the service device forms a service module which can be easily and quickly installed, can be mounted in a functionally reliable manner on site, and can also be dismantled for maintenance.

A particularly advantageous functionally integrated solution is obtained when the at least one injection nozzle element or at least one injection nozzle element is arranged and/or supported directly on the service platform, preferably on an assembly wall region of the service platform.

The service platform may further have an assembly wall, for example integrally formed with the service platform or rigidly connectable or connected to the service platform as a separate component, which assembly wall is preferably an assembly wall projecting at an angle from the service platform. The injection nozzle element is preferably arranged and/or supported on the assembly wall. In the case of a rear, connection-side end of the injection nozzle element which is located or arranged outside the tank inner chamber, the injection nozzle element can then alternatively or additionally be guided very easily with its end having the injection nozzle through the assembly wall into the tank inner chamber and held on the assembly wall. In the case of a completely internal injection nozzle element, this is not necessary and a simple fixing or holding on an assembly wall region of the service platform, for example on the side of the assembly wall facing the tank inner chamber, is sufficient.

The service platform and/or the assembly wall are preferably made of a metal, in particular of a steel material, most preferably of a stainless steel material. Depending on the size and surface extent of the service platform and/or the assembly wall, the latter can have a wall thickness of up to several centimeters to form a stable, walkable service platform or assembly wall.

A particularly preferred embodiment is one in which the assembly wall projects upwardly from the service platform, preferably from an approximately horizontal assembly wall attachment region of the service platform, in the direction of the vertical axis of the tank, the assembly wall forming, with its upper edge region, which lies above the injection nozzle element in the direction of the vertical axis of the tank, at least a partial region of the roof connection region, preferably at least a partial region of a film roof connection region. Such a design of the service platform makes it possible to attach an injection nozzle element in a particularly advantageous manner to an assembly wall projecting upwardly from the service platform and is also characterized in particular by easy accessibility for operating personnel. In addition, this upwardly projecting assembly wall is also suitable for a particularly simple and advantageous attachment of an adjoining roof, in particular a foil roof, it then being simultaneously ensured that the injection nozzle element is located below the roof and thus in the tank inner chamber. In addition, such an assembly wall, which projects upwardly, creates a relatively high attachment possibility for an injection nozzle element, which makes it possible to easily apply a liquid jet coming from above to the surface of the floating layer. This also makes it possible to achieve long ranges in a simple manner.

According to another particularly preferred embodiment, the service platform, which is preferably formed by a walkable and/or level platform plate, is designed in the manner of a trapezium, preferably an isosceles trapezium. A first base side, preferably as a longer base side, adjoins the tank wall, in particular the tank side wall, while a second base side, preferably as a shorter base side, lies opposite the first base side. The two base sides are connected by obliquely extending leg sides, it also being provided that the assembly wall extends over the second base side and at least in some regions over the two leg sides, in particular in such a way that the assembly wall slopes from the second base side towards the first base side, preferably slopes obliquely downwardly. With such a geometrical structure of a service platform in the manner of a trapezium with, relative to the mounted position, an assembly wall lying relatively far inwardly in the direction of the fermenter tank, a large-area service platform is provided which can be integrated excellently in roof structures, in particular in foil roofs, and which can also be supported over a large area on the tank, in particular on a tank side wall.

For the reasons mentioned above, it is particularly advantageous if the injection nozzle element is held on the assembly wall in the region of the second base side, for example, if it is held on and passed through the assembly wall.

In principle, however, it would also be possible for at least one injection nozzle element or at least one injection nozzle element not to be arranged on the service platform itself, but on a tank wall, in particular on a tank side wall, as an assembly wall, which may be the case, for example, if no service platform should be provided.

The end of the injection nozzle element comprising the injection nozzle is preferably coupled to an adjusting device which can be actuated from outside the fermenter tank and by means of which the position of the injection nozzle in the tank inner chamber can be adjusted, in particular can be changed. In this way, the orientation, angle and point of impingement of the liquid jet can be adjusted or changed advantageously.

Specifically, for this purpose, the injection nozzle can be attached to the injection nozzle element by means of an elastic, sleeve-shaped or tubular intermediate piece and connected to a guide rod of the adjusting device, it then preferably being provided, in this case, that the guide rod is rigidly attached to an upper side of the injection nozzle in relation to the direction of the vertical axis. The guide rod itself is then preferably guided with play and gas-tightly through an assembly wall region to the outside of the fermenter tank and is held there in a slotted guide which allows the guide rod to be displaced in the direction of the vertical axis and/or transversely to the direction of the vertical axis and/or in the longitudinal direction of the guide rod. This results in great flexibility with regard to the specific arrangement of the injection nozzle. The elastic, tubular intermediate piece enables the relative displacement of the injection nozzle, which can have a nozzle opening with a diameter between, for example, 30 mm and 90 mm, relative to a fixed region of the injection nozzle element.

According to a specific embodiment, a pressure line leading away from the delivery pump can be connected to the connection-side end of the injection nozzle element outside or inside the fermenter tank. This makes it possible to arrange the delivery pump at a desired location, spaced apart from the injection nozzle element. The delivery pump naturally has an intake side, by means of which the substantially liquid substrate accommodated in the fermenter tank can be drawn in or extracted.

For the delivery pump, especially in conjunction with an arrangement of the connection-side end of the injection nozzle element outside the fermenter tank, there are different arrangement possibilities, which will be explained in more detail below:

Thus, according to a particularly preferred first embodiment, the pressure line can be led from the connection-side end of the injection nozzle element through a pressure line feedthrough, preferably through a pressure line guide in the service platform, to an internal delivery pump arranged in the tank inner chamber. With such an internal arrangement of the delivery pump, said pump can be easily arranged exactly where the desired substrate can be extracted. At this juncture, it is further advantageous if the pressure line is formed by a rigid pressure pipe guided in the fermenter tank, it then being further preferably provided that the pressure pipe is supported and/or mounted in the region of the pressure line feedthrough and/or in the tank inner chamber on the tank wall side, in particular on the tank bottom side. This results in an overall stable structure, so that the internal delivery pump can be connected and/or held in a functionally reliable manner to/on the rigid pressure pipe. Such a structure with a rigid pressure pipe is, of course, also suitable for connection to a rear connection-side end of the injection nozzle element located in the tank inner chamber.

Alternatively, the pressure line, preferably at least one partial region of the pressure line located in the tank inner chamber, can be designed as a pressure line which is variable in shape and/or length, in particular as a flexible or telescopic pressure line. This is particularly advantageous if the internal delivery pump is guided height-adjustably along a delivery pump guide mast arranged in the fermenter tank and oriented in the direction of the vertical axis of the tank. Such a design with a height-adjustable delivery pump allows the delivery pump to be arranged at different heights in an advantageous way. In addition, the height adjustment enables easy maintenance of the delivery pump, as it can be easily moved out of the substrate. The delivery pump guide mast can, for example, be supported and/or held on the service platform or at the same time can also be supported and/or held in the tank inner chamber on the tank wall side, for example on the tank bottom side. Such a design is of course suitable for connection to a rear, connection-side end of the injection nozzle element located in or outside the tank inner chamber.

Particularly preferred is an embodiment in which the service platform, preferably immediately adjacently to the pressure line feedthrough in the service platform, has a delivery pump service opening, in particular for entry and/or access to the internal delivery pump, which opening can be closed gas-tightly by means of a covering device.

According to another alternative embodiment, the pressure line can be led from the connection-side end of the injection nozzle element to an external delivery pump arranged outside the fermenter tank, the intake side of which pump has at least one intake line which is led to an intake port in the tank wall, in particular in the tank side wall, or through the tank wall, in particular through the tank side wall, into the interior of the fermenter tank. The advantage of such an external delivery pump arranged outside the fermenter tank is in particular its easy accessibility. In this case, however, an intake port to the inside of the fermenter tank must be made. For this purpose, according to another particularly preferred embodiment, it may be provided that a plurality of intake ports arranged at different heights as seen in the direction of the vertical axis of the fermenter tank are arranged on the tank side wall, in particular intake ports arranged in the direction of the vertical axis substantially in rows one above the other and spaced apart from one another, which can be connected to an intake line of the external delivery pump or are connected, preferably in valve-controlled fashion. This makes it possible to remove substrate from different heights or to connect a plurality of intake lines simultaneously, for example for different injection nozzle elements.

At this juncture, it should be expressly mentioned again that external delivery pumps and internal delivery pumps can also be present in parallel, for example in conjunction with a plurality of injection nozzle elements or also with one injection nozzle element, for which, however, corresponding changeover valves would then have to be provided.

In accordance with another particularly preferred embodiment, the service platform has, in particular in addition to the delivery pump service opening, a service opening for the agitator that can be closed by means of a covering device, preferably gas-tightly, through which service opening an agitator guided on an agitator guide mast height-adjustably is accessible for maintenance and service works and/or can be moved, preferably substantially gas-tightly, out of the fermenter tank and back into the fermenter tank. This again results in a significant advantage with regard to being able to perform maintenance and service works on the agitator easily, and the agitator can be easily moved into the region of the agitator service opening and preferably also out of the fermenter tank.

The covering device sealing a service opening gas-tightly may be formed by at least one cover and/or by a mast housing projecting upwardly away from the service opening and forming a receiving space for an upper part of the guide mast in question. For example, in accordance with a particularly preferred refinement, it may be provided here that the guide mast, i.e. the delivery pump guide mast and/or the agitator guide mast, relative to the tank direction of the vertical axis, is led upwardly out of the fermenter tank via the mast upper part through the service opening, the service opening being covered gas-tightly by a cover and an adjacent mast housing projecting beyond the plane of the cover. The mast housing has at least one side wall, is open at the bottom towards the fermenter tank and forms, preferably with a cover wall of a mast housing which for example is box-shaped, a bearing for the mast upper part. The side wall or at least one side wall of the mast housing is designed as an openable maintenance wall, and the cover, which is likewise openable, adjoins in the lower region of the openable maintenance wall, so that the maintenance wall and the cover can be opened. This allows the agitator or alternatively the delivery pump to be lifted out of the fermenter tank above the level of the service opening in question.

Furthermore, around the service opening there is preferably arranged a sealing element which, in the sealing position, projects downwardly in the form of a shaft into the interior of the fermenter tank and which, at least during maintenance and service works, dips into the liquid substrate to be fermented, which is accommodated in the fermenter tank, and separates the gas phase region annularly enclosed by the sealing element below the openable service opening and above the substrate gas-tightly from the remaining gas phase region of the fermenter tank inner chamber. With such a design, the maintenance and service works on a delivery pump brought into the region of the service opening or on an agitator brought into the region of the service opening can be carried out in a particularly functionally reliable manner, as it is ensured that no undesired large quantities of gas can escape via the service opening.

It is particularly preferred in conjunction with such a structure that the sealing element is formed by a rigid, non-displaceable and inflexible collar in the form of a pipe socket which permanently projects from the service opening towards the inner chamber of the fermenter tank.

With such a sealing element, a further functional integration is thus created, in conjunction with the service platform, on a separately installable component that can be used flexibly as a service module and can itself also be easily replaced or dismantled again.

This service platform can also have at least one outer edge region which lies against a tank side wall in a gas-tight contact connection and is rigidly attached there. Here, for example, the outer edge region can be rigidly attached to the tank side wall by means of a screw connection. The screw connection ensures a detachable connection that also allows the service platform to be easily dismantled again, for example in conjunction with replacement and maintenance works on the service platform.

As already mentioned above, it is particularly advantageous to support the service platform, especially large-area service platforms, from below using a support device. This support device can be formed, for example, by supports which act on the underside of the service platform and are guided, for example, to the tank side wall and/or to the tank bottom in order to support the service platform there.

In the event that the roof should be a foil roof, it is preferably provided that the foil roof, in particular a foil roof edge region, is in particular wedged gas-tightly by means of a clamping connection between a clamping region, in particular an edge flange of the service platform, and a clamping strip which can be detachably connected.

Furthermore, according to the invention, a service device or a service module for mounting on a tank wall of a biogas plant fermenter tank is claimed, having a walkable service platform which can be arranged in the region of a roof, in particular a foil roof, of a fermenter tank, and which can be fixed, preferably can be detached and gas-tightly fixed, to a tank wall, in particular to a tank side wall of the fermenter tank, by means of at least one connecting element, and which has a roof connection region to which the roof, preferably a foil roof, can be connected. The service platform, which is preferably formed by a walkable and/or level platform plate, has an agitator service opening which can be closed by means of a covering device, preferably gas-tightly, and through which an agitator is accessible and/or can be moved out of the fermenter tank and back into the fermenter tank for maintenance and service works. The agitator and/or the associated agitator guide mast also form components of the service device in accordance with a particularly preferred embodiment. In accordance with the invention, at least one injection nozzle element of an injection device is also arranged and/or held on the service platform, preferably on an assembly wall region of the service platform, the injection device also having at least one delivery pump, preferably also forming part of the service device, by means of which delivery pump injection liquid can be drawn in or extracted, preferably from the substrate of the fermenter tank or from another fermenter tank of the biogas plant, and can be conveyed to the at least one injection nozzle element.

It is preferably provided that the at least one injection nozzle element, in the assembled state, projects into the tank inner chamber by means of a front end having an injection nozzle, preferably gas-tightly, and the injection liquid can be injected into the fermenter tank, while a rear, connection-side end of the injection nozzle element is arranged outside the tank inner chamber. Alternatively, however, it is also possible that the at least one injection nozzle element in the assembled state is arranged completely in the tank inner chamber.

In accordance with the invention, such a service device thus forms a service and assembly module which, in addition to at least one functional part of a stirring unit, also has at least one functional part of an injection device, so that a highly integrative service device of flexible design and containing a plurality of functional units is produced, which enables simple and functionally reliable maintenance of the individual functional units. In addition, there is also a high degree of flexibility with regard to the possible applications, for example in conjunction with retrofit solutions or the like.

With regard to the further advantages of this service device according to the invention, reference is made to the explanations provided above, which naturally apply analogously. The same also applies analogously to the dependent claims relating to the service device, which are referred back to the service device according to the invention and which each contain preferred embodiments. Here, too, reference is made to the comments provided above with regard to the resulting advantages. In conjunction with the service device, the expression "in the direction of the vertical axis" means a reference to the assembled state of the service device or service platform, i.e. an orientation in the tank direction of the vertical axis.

Furthermore, a method is also claimed. The advantages resulting in conjunction with the execution of the method according to the invention are identical to those of the biogas plant fermenter tank, as already described above. In this respect, reference is made to the explanations provided there so as to avoid repetition.

In addition, a biogas plant with at least one biogas plant fermenter tank is claimed.

The invention will be explained in greater detail below by way of example by means of drawings, in which:

FIG. 1 shows a basic schematic sketch of a possible design of a biogas plant fermenter tank in order to illustrate the basic principle according to the invention;

FIG. 2 schematically shows a further basic sketch as a plan view of a fermenter tank with stirring devices and injection nozzle elements arranged therein merely by way of example;

FIG. 3 schematically shows a perspective partial view of a biogas plant fermenter tank with a service platform of a service device with an embodiment in which the delivery pump is arranged in the fermenter tank inner chamber on a rigid pressure pipe;

Figure 1:
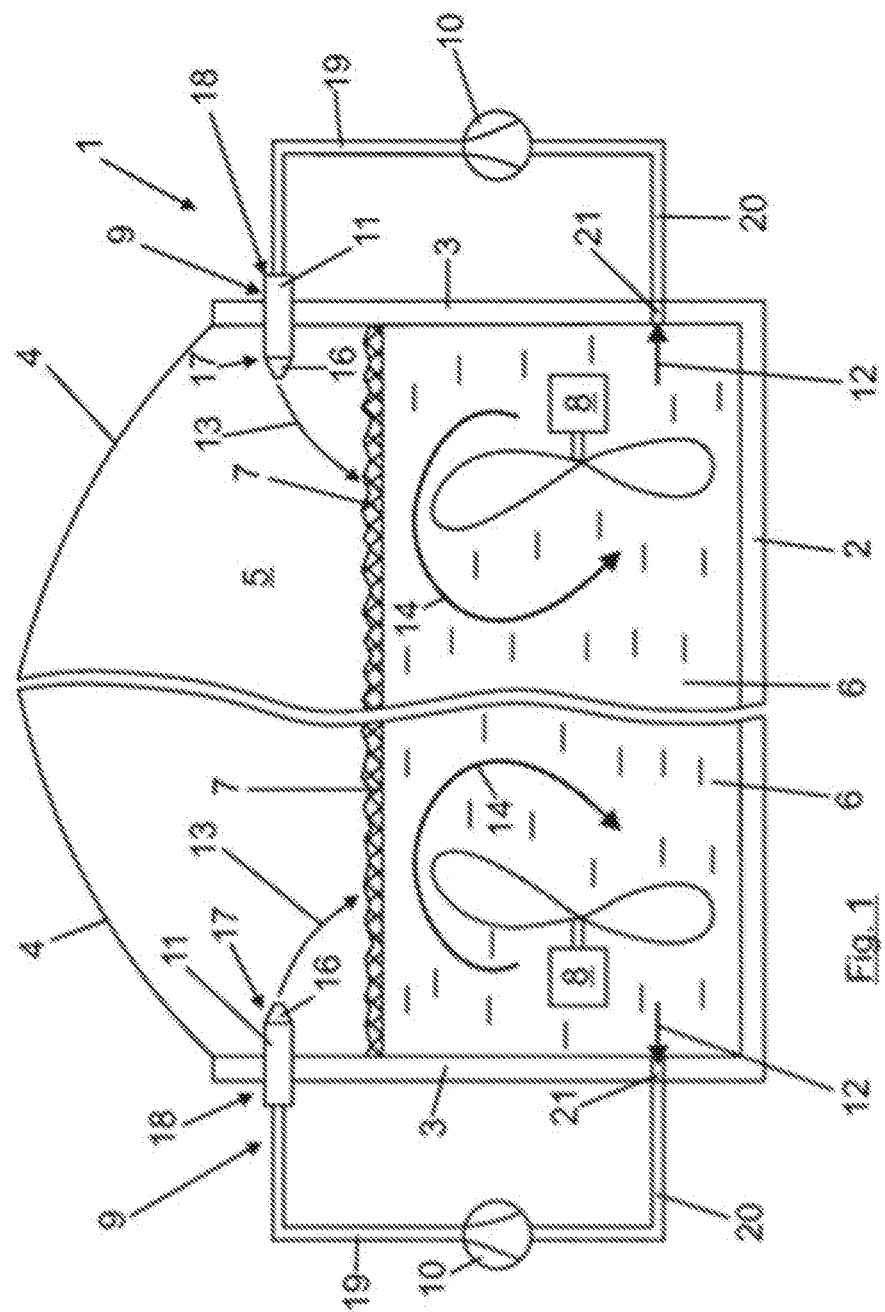
FIG. 1 shows an exemplary and schematic basic sketch, by means of which the structure and the operating principle of a biogas plant fermenter tank according to invention will be explained in greater detail by way of example.

In FIG. 1, a biogas plant fermenter tank 1 of a biogas plant (not shown further), which may also have at least one further fermenter tank in addition to the biogas plant fermenter tank 1, is shown, i.e. the biogas plant fermenter tank 1 can be a pre-fermenter tank, a main fermenter tank, or a post-fermenter tank of a biogas plant. This fermenter tank 1 has a tank bottom wall 2 as well as a preferably circular cylindrical tank side wall 3 and is covered on its top side and thus on the ceiling side with a foil roof 4, which is only shown here schematically and in principle. In this regard, the fermenter tank 1 is of a conventional design.

The tank inner chamber 5 contains a substantially liquid substrate 6 to be fermented, which is formed, for example, by a liquid, such as liquid manure, which contains solids, such as straw, which have a relatively strong tendency to float, so that a floating or cover layer 7, which is only shown here schematically, forms on the surface of the substrate 6 and routinely has a fissured surface structure.

In the tank inner chamber 5, two mechanical stirring devices 8 forming stirring units with stirring blades are arranged here, as an example. These stirring devices 8 (of course, it is also possible to provide only one single stirring device 8) are designed and arranged in the tank inner chamber 5 in such a way that, by means of these stirring devices, the substrate 6 is substantially or preferably completely homogenized and/or mixed only in the region below the floating layer and without stirring the floating layer into the substrate.

Furthermore, an injection device 9 is provided here, which here has only two delivery pumps 10, as an example (it is also possible that only one delivery pump 10 is provided), by means of which a specific amount of substrate is extracted from the fermenter tank 1 as injection liquid. Alternatively or additionally, the substrate can also be extracted from any other fermenter tank of an associated biogas plant in a manner not shown here. In this case, the at least one delivery pump is then arranged in or on the other fermenter tank in such a way that the substrate there can be extracted.

The injection device 9 further has an injection nozzle element 11 which is fluidically connected to a corresponding delivery pump 10 and by means of which the injection liquid 12 extracted by means of the at least one delivery pump can be injected into the fermenter tank 1 or into the tank inner chamber 5 in such a way that, relative to a direction of the vertical axis of the tank, it impinges as a liquid jet 13 from above onto the surface of the floating layer 7 of the substrate 6 and wets the latter. As already explained in conjunction with the delivery pump 10, the arrangement of, here, a total of two injection nozzle elements 11 is only to be understood as an example, and of course there could also be only a single injection nozzle element 11. It is also possible to provide only one delivery pump 10, which feeds a plurality of injection nozzle elements 11. In principle, only one single injection nozzle element 11 could be provided, which is fluidically connected to a plurality of delivery pumps 10, in which case the delivery pumps 10 can then, if necessary, draw in substrate from different regions or different heights, as viewed in the direction of the vertical axis of the tank, and/or from different fermenter tanks of the biogas plant.

By wetting the floating layer 7 with substrate from the fermenter tank 1, it is advantageously achieved that the floating layer 7 itself is also incorporated in the process of fermentation and thus biogas production, so that it does not have to be broken up and stirred, as has been the case until now. The additional arrangement of at least one stirring device 8 simultaneously achieves a substantially complete mixing and thus homogenization of the substrate below the floating layer 7, as shown schematically by the arrows 14, which also contributes to achieving a high biogas yield. The particular advantage of operating the stirring device 8 without the need to break up or stir in the floating layer 7 is that the substantially complete homogenization or mixing of the liquid substrate 6 alone, i.e. without floating layers, can be achieved with relatively little energy expenditure, and therefore the energy consumption of the stirring device 8 actuated in accordance with the invention is considerably lower than that of a stirring device by means of which floating layers are broken up and stirred in.

The liquid jet 13 of an injection nozzle element 11 is adjusted here depending on the nozzle opening and the delivery pressure applied via the delivery pump 10, in such a way that a desired wetting of the surface of the floating layer 7 is achieved, in particular in such a way that, preferably, the floating layer 7 is not completely destructed. It is particularly preferred that the surface of the floating layer 7 is only acted upon in such a way that it becomes more fissured in order to provide an enlarged surface area for attack by the bacteria from the substrate sprayed on.

Figure 2:
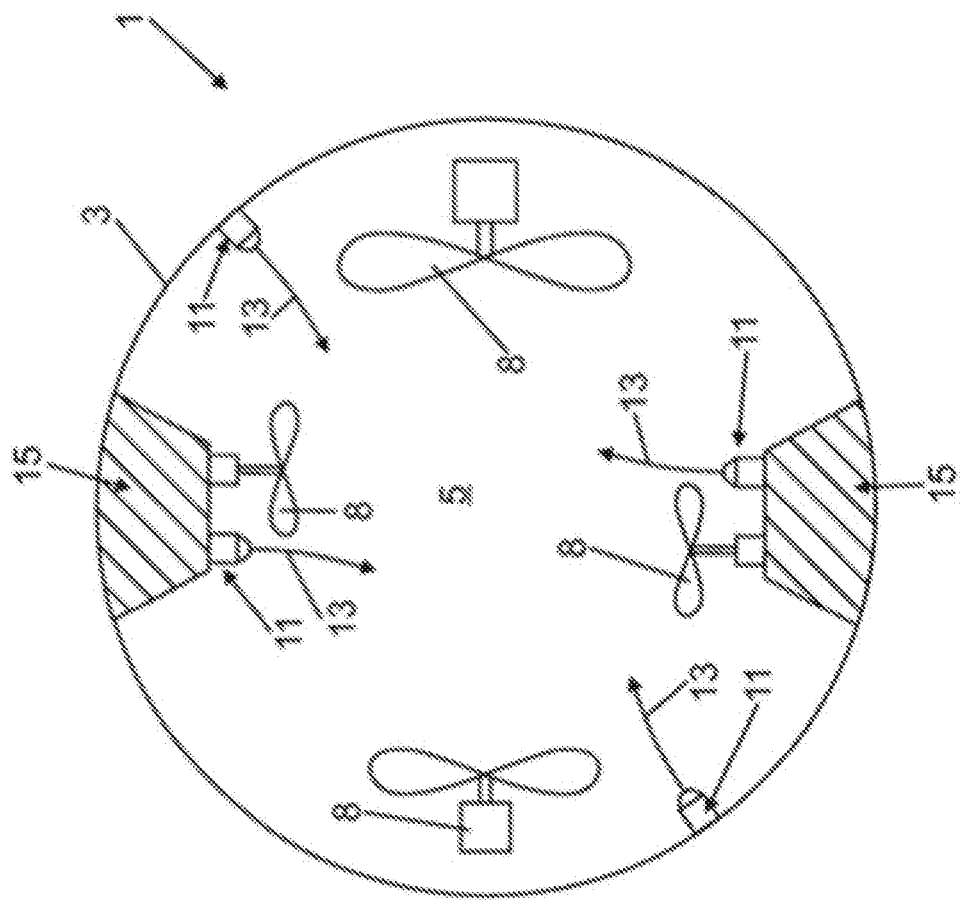

As can be seen in FIG. 1, there are different ways of arranging an injection device 9 and a stirring device 8. As shown in FIG. 2 only schematically and in principle, depending on the size of a fermenter tank 1, preferably viewed in the circumferential direction, a plurality of identical and/or different stirring devices 8 or injection nozzle elements 11 can also be arranged spaced apart from one another. FIG. 2 further shows schematically that the individual stirring devices 8 can also be of different sizes and thus can be able to achieve different stirring performances. The stirring devices 8 can be, in principle, separate stirring units, which are introduced into the tank inner chamber 5 as separate units from the side or from above, in each case in relation to the direction of the vertical axis of the tank. Alternatively, these stirring devices 8 can also be part of a service device 15, as described below in conjunction with the other exemplary embodiments.

Similarly, the injection devices 9, as shown in conjunction with FIG. 2, may be at least partly a component of such a service device 15 or, as also shown in FIG. 1, may be formed by separate units installed independently of such a service device 15, for example on the tank side wall 3, in such a way that a front end of the injection nozzle element 11, which has an injection nozzle 16, projects, preferably gas-tightly, into the tank inner chamber 5, while a rear, connection-side end 18 of the injection nozzle element 11 lies or is arranged outside the tank inner chamber 5 and is prepared there for connection of a pressure line 19 of the delivery pump 10 and is easily accessible. This pressure line 19 can be designed as a flexible or rigid pressure line, just as the intake line 20 upstream of the delivery pump 10 can be designed to be flexible or rigid. The intake line 20 can either be led to an intake port 21 in the tank side wall 3 or it can also be led through the tank side wall 3 into the interior of the fermenter tank 1.

In the schematic basic sketch of FIG. 1, the delivery pump 10 is only shown by way of example as an external delivery pump 10 located outside the fermenter tank 1. However, as will be explained in more detail in the following drawings, this delivery pump 10 can also be located inside the tank inner chamber 5.

FIGS. 3 and 4 show a particularly preferred embodiment or variant according to the invention with a service device 15, which has a walkable service platform 22 which can be arranged in the region of a foil roof 4, only drawn in a very schematic manner by dashed lines in FIG. 3, and which is formed here, again merely by way of example, by a walkable and level platform. This service platform 22 has an outer edge region 23, which, merely by way of example, rests here in a gas-tight contact connection on the tank side wall 3 and is attached there removably or rigidly, for example by means of a screw connection. As can be seen in particular from FIG. 4, but only very schematically there, the service platform 22 can also be supported from below on its underside with a support device formed by a support frame 24, with the support frame 24 being supported here, merely by way of example, on the inside of the tank side wall 3.

The service platform 22 is designed here, by way of example, in the manner of a trapezium, more specifically preferably an isosceles trapezium, with a first base side forming the longer base side, which forms the outer edge region 23 and adjoins the tank side wall 3. The second base side 26 opposite the first, longer base side 25 forms the shorter base side, and the two base sides 25, 26 are connected by obliquely extending leg sides 27, 28.

As can be further seen from the combination of FIGS. 3 and 4, the service platform 22 has an assembly wall 29 projecting upwardly from it in the direction of the vertical axis of the tank, in this case at right angles, for example. This assembly wall 29 extends here only by way of example over the entire second base side 26 and substantially completely over the two leg sides 27, 28, with the height of the assembly wall sloping downwardly from the second base side 26 to the first base side 25.

As shown only very schematically and by dashed lines in FIG. 3, the assembly wall with its upper edge region 30 forms the, or at least a part of the, foil roof connection region 31 on the service platform side, to which the foil roof 4 is preferably fixed gas-tightly and preferably by means of a detachable clamping connection.

As can also be seen from FIGS. 3 and 4, the injection nozzle element 11 is here, by way of example, held in the region of the second, shorter base side 26 on the assembly wall 29 and passed through it in such a way that the front end, which has the injection nozzle 16, projects, preferably gas-tightly, into the tank inner chamber 5, while the rear, connection-side end 18 of the injection nozzle element 11 lies outside the tank inner chamber 5 above the service platform 22 and is thus very easily accessible for the connection of a pressure line 19.

In the exemplary embodiment of FIGS. 3 and 4, the pressure line 19 is designed as a rigid pressure line, which, starting from the connection-side, rear end of the injection nozzle element 11, is led through a pressure line feedthrough 32 in the service platform to an internal delivery pump 10 arranged in the tank inner chamber.

The pressure line 19 formed by a rigid pressure pipe is supported or held here in the region of the pressure line feedthrough 32 and also, for example, on the bottom side of the tank.

As can be seen in particular in FIG. 4, the internal delivery pump 10 is attached here directly to the rigid pressure pipe as a pressure line 19 and is held so that the delivery pump 10 draws in the injection liquid directly via its intake side and delivers it via the pressure pipe as pressure line 19 to the injection nozzle element 11.

The injection nozzle 16 is attached to the injection nozzle element by means of an elastic, tubular intermediate piece (FIGS. 3 and 4) 33, which is only shown here in an extremely schematic manner, and which can be an elastomer hose, and is connected to a guide rod 34 of an adjusting device 35, the guide rod 34, in this case, acting on or being attached to the top side of the injection nozzle 16, relative to the direction of the vertical axis of the tank.

The guide rod 34, which is not shown in detail here, is guided with play and via an elastomer sleeve in a gas-tight manner through an assembly wall region to the outside of the fermenter tank 1 and is mounted there in a slotted guide 36 of the adjusting device 35, in such a way that a displacement of the guide rod 34 in the direction of the vertical axis and/or transversely to the direction of the vertical axis and/or in the longitudinal direction of the guide rod is possible, and thus the front end 17, which has the injection nozzle 16, can be arranged in different positions, for example in order to adjust or change the radiation angle.

Figure 3:
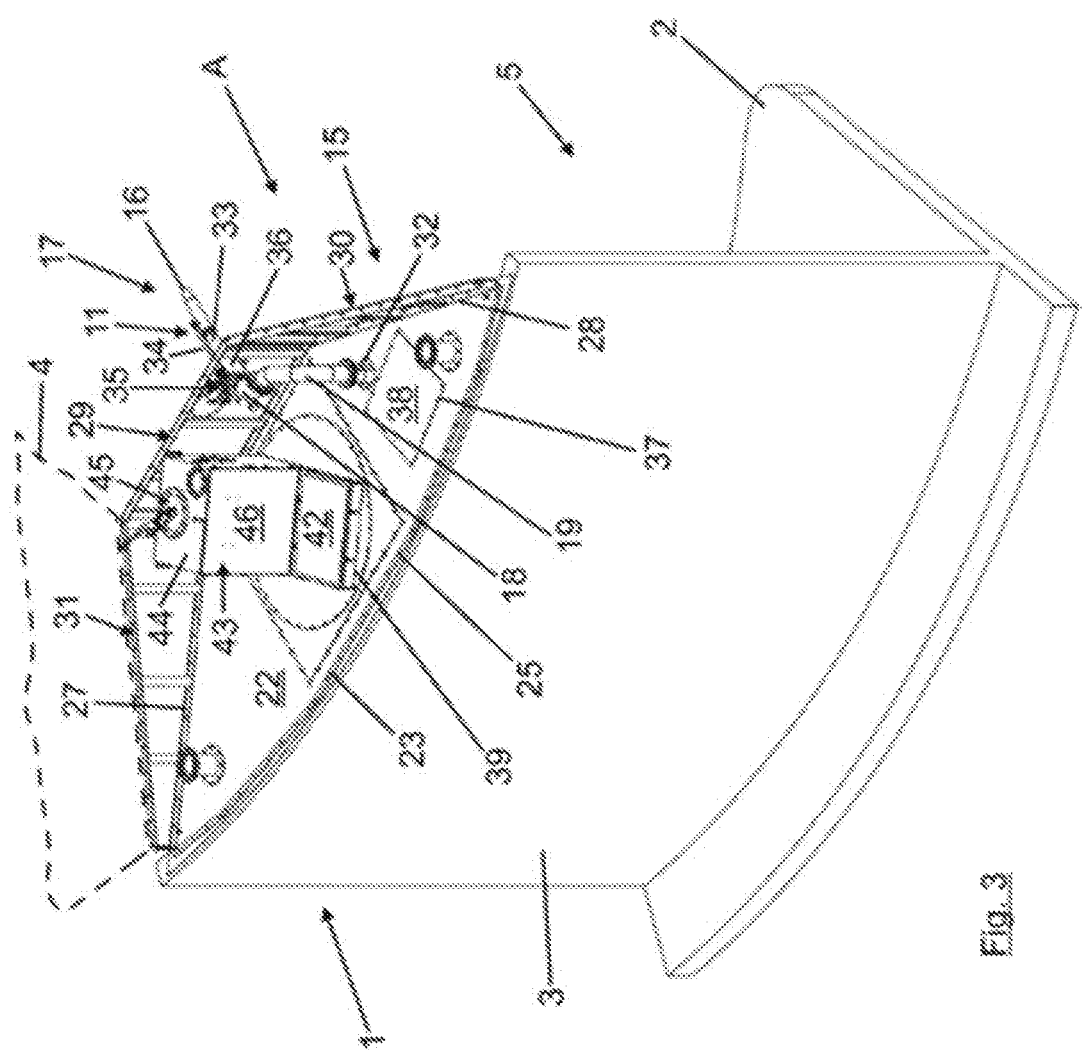

As can also be seen in particular in FIG. 3, the service platform 22 has a delivery pump service opening 37, in particular as an inspection opening, which is closed gas-tightly by means of a cover 38 as a covering device, in particular directly adjacently to the pressure line feed-through 32 in the service platform 22. If the cover 38 is removed, entry and/or access to the internal delivery pump 10 is possible via the delivery pump service opening 37.

As can also be seen from the overview of FIGS. 3 and 4, the service platform 22 also has an agitator service opening 39 which can be closed gas-tightly by means of a covering device described in more detail below, through which opening a stirring device guided on a stirring device guide mast 40 height-adjustably is accessible as stirring device 8 for maintenance and service works or can be moved out of the fermenter tank 1 and back into the fermenter tank 1, preferably substantially gas-tightly. The stirring device 8 is designed here by way of example as a submersible agitator with stirring blades.

At this juncture, it should be mentioned that all stirring devices can be operated electrically, pneumatically or hydraulically in the known manner. The same applies to the delivery pumps 10.

In conjunction with the height-adjustably guided submersible agitator, it should also be mentioned that the height adjustment can be carried out in a manner known per se, for example using a cable winch or the like. In FIG. 4 only the traction cable 41 acting on the submersible agitator is shown, as an example.

Figure 4:
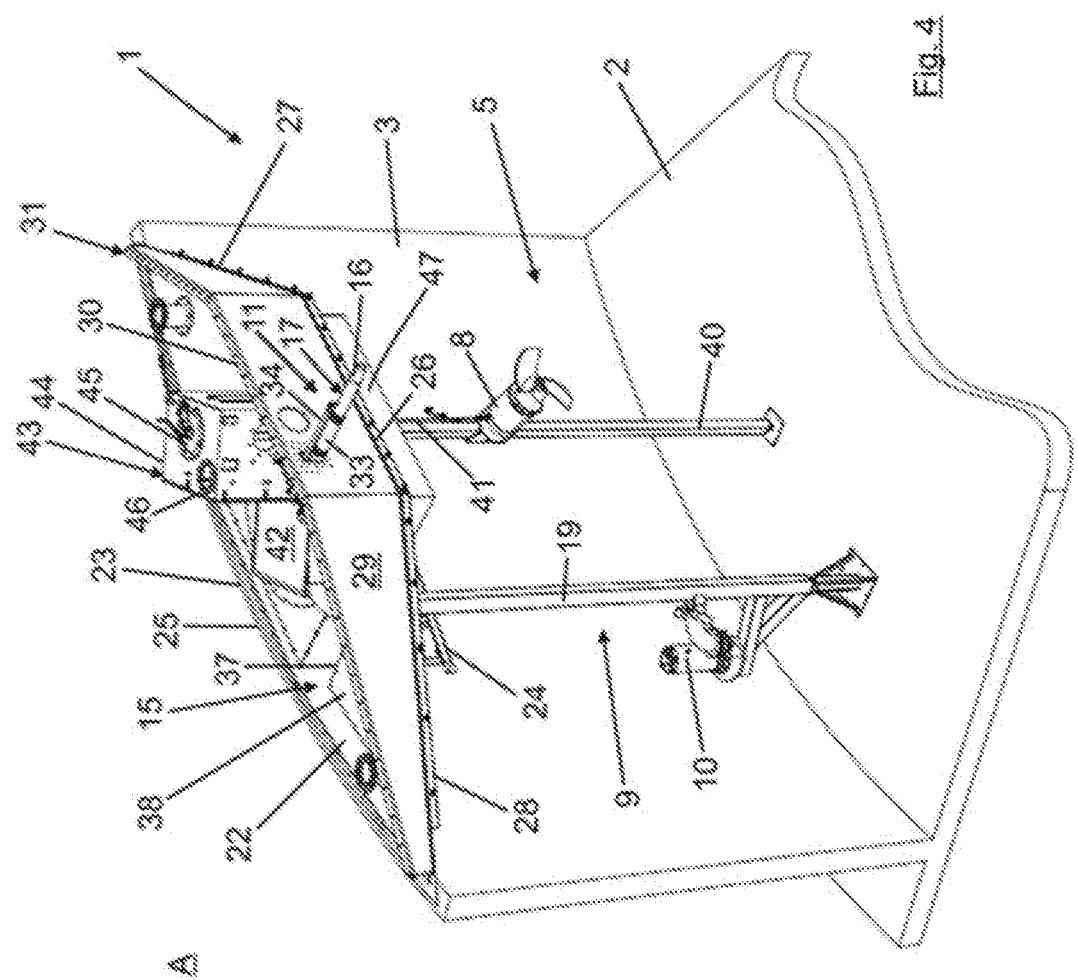
FIG. 4 shows a view corresponding to the arrow A in FIG. 3.

As can also be seen from FIGS. 3 and 4, the agitator guide mast 40, in relation to the direction of the vertical axis of the tank, is guided upwardly with an upper part of the mast through the agitator service opening 39 out of the fermenter tank 1, with the agitator service opening 39 being covered gas-tightly by a cover 42 and an adjacent mast housing 43 which projects beyond the plane of the cover 42. Here the mast housing 43 has a plurality of side walls, is open at the bottom towards the tank inner chamber 5 and forms a bearing 45 for the mast upper part in a cover wall 44. The side wall 46 of the mast housing 43 is designed as an openable maintenance wall, which is adjoined in the lower region by the cover 42, which is likewise openable, so that the openable side wall (maintenance wall) 46 and the cover 42 can be opened and the stirring device 8 can be lifted upwardly above the level of the stirring device service opening 39 out of the tank inner chamber 5.

As shown in particular in FIG. 4, around the agitator service opening 39 there is arranged a sealing element as a gas skirt 47 which, in the sealing position, projects downwardly in the form of a shaft into the fermenter tank inner chamber 5 and which—in a manner not shown here—at least during maintenance and service works, dips into the liquid substrate that is accommodated in the fermenter tank 1 and is to be fermented, and gas-tightly separates the gas phase region annularly enclosed by the gas skirt below the openable agitator service opening 39 and above the substrate from the remaining gas phase region of the tank inner chamber 5. The gas skirt 47 is here, for example, formed by a rigid, non-displaceable and inflexible collar in the form of a pipe socket which permanently projects from the agitator service opening 39 in the direction of the fermenter tank inner chamber 5.

In conjunction with the delivery pump service opening 37 and the agitator service opening 39, different possibilities for the design of a covering device for a service opening are explained here in greater detail, by way of example. It goes without saying that the agitator service opening 39 can of course also only be sealed gas-tightly by a cover, as has been explained in conjunction with the delivery pump service opening 37.

On the other hand, instead of the cover 38 for the delivery pump service opening 37, a cover 42 and mast housing 43 can also be provided, as has been explained in greater detail in conjunction with the agitator service opening 39. This is particularly advantageous if, as shown only very schematically in FIG. 5, the internal delivery pump 10 is also designed as a functional part that is height-adjustably guided on a delivery pump guide mast 48 in the direction of the vertical axis of the tank, because then the delivery pump 10 can also be lifted upwardly above the level of the delivery pump service opening 37. In this case, the pressure line 19 or at least a partial region of this pressure line 19 lying in the tank inner chamber 5 is then also designed as a pressure line which is variable in shape and/or length, in particular as a flexible or telescopic pressure line. The height adjustment of the delivery pump 10 along the delivery pump guide mast 48 can then be carried out here in the same way as the height adjustment of a submersible agitator on the agitator guide mast 40, for example by means of a traction cable that can be wound or unwound on a cable winch.

Figure 5:
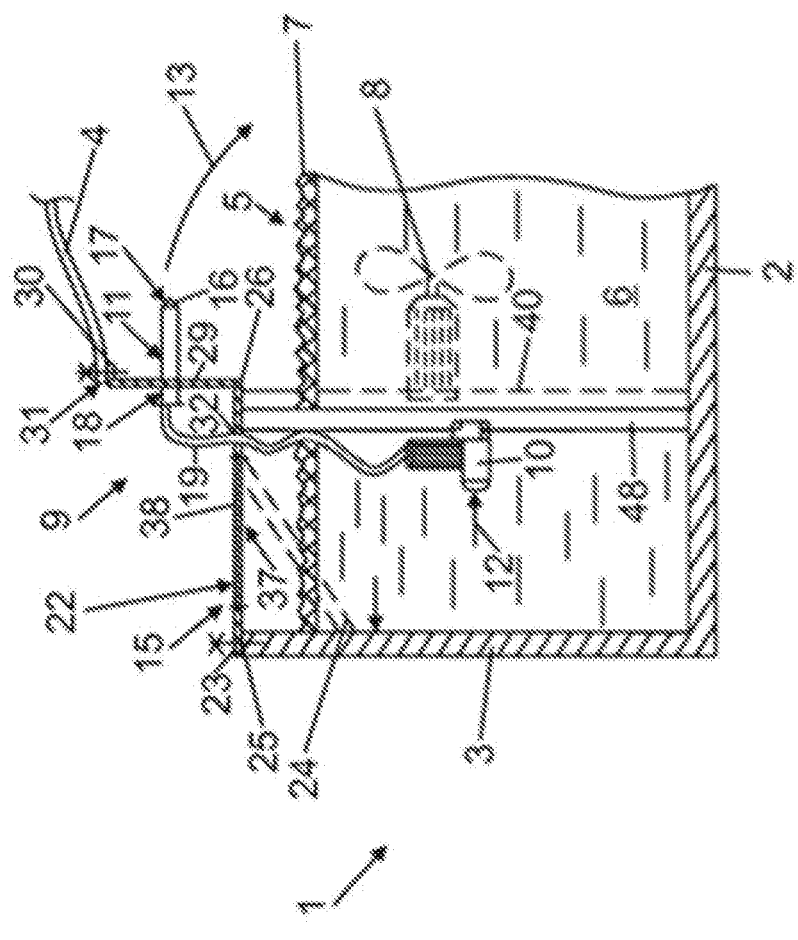
FIG. 5 shows a design that is alternative to the embodiment according to FIG. 3 and FIG. 4, with a flexible pressure line and a delivery pump held height-adjustably along a delivery pump guide mast.

In FIG. 5, however, the displaceable variant of the internal delivery pump 10 is shown here in conjunction with a cover 38 as a covering device, as explained above in conjunction with FIGS. 3 and 4.

In FIG. 5, on the one hand the support frame 24 is shown by a dashed line, only very schematically and basically, and an agitator guide mast 40 with a submersible agitator as stirring device 8 is also shown schematically and by a dashed line. For reasons of clarity, however, no mast housing 43 for this agitator guide mast 40 is shown in FIG. 5.

The explanations just given show that there are various possibilities for designing the service platform 22 of the service device with a covering device for service openings, with the corresponding desired variant being selected depending on the application and purpose. It should also be mentioned here, merely for the sake of completeness, that it would of course also be possible in principle to provide a cover with a mast housing in conjunction with a delivery pump 10, which in particular is height-adjustably guided on a delivery pump guide mast 48, and for the agitator service opening 39 merely a cover corresponding to the cover 38 of FIGS. 3 and 4.

It goes without saying that a gas skirt 47 can of course also be provided in conjunction with the delivery pump service opening 37, especially in conjunction with the height-adjustable delivery pump variant shown in FIG. 5, even though this is not explicitly shown.

Figure 6:
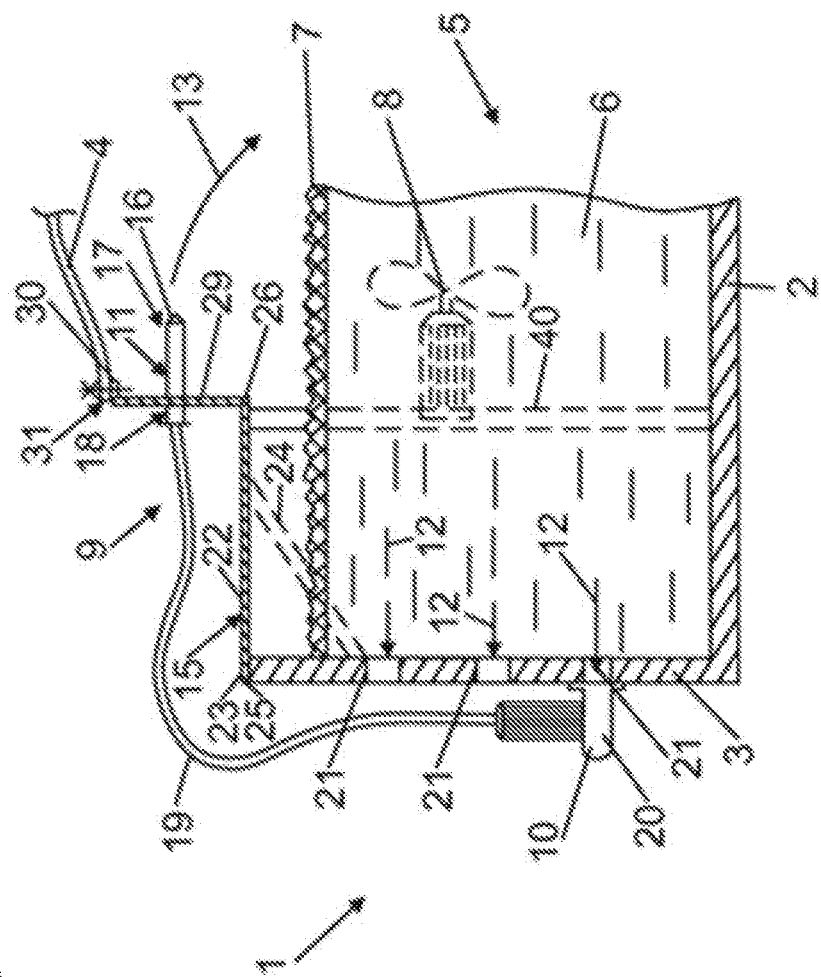
FIG. 6 shows a schematic basic sketch of another alternative embodiment, in which the delivery pump is located outside the fermenter tank inner chamber.

FIG. 6 shows a further alternative embodiment in which the pressure line 19, preferably in the form of a pressure line of variable shape and/or length, for example as a flexible pressure line, is led from the connection-side rear end 18 of the injection nozzle element 11 to an external delivery pump arranged outside the fermenter tank 1 (see also FIG. 1), the intake side of which pump has an intake line 20 which is led to an intake port 21 in the tank side wall 3. As further illustrated in FIG. 6, the tank side wall may be provided with a plurality of intake ports 21 arranged at different heights in the direction of the vertical axis of the tank, more specifically in particular in the direction of the vertical axis substantially in a row of intake ports 21 arranged one above the other and spaced apart from one another. These intake ports 21 may be connected to the intake line 20 of the external delivery pump 10 so that the delivery pump can be arranged at different heights with respect to the substrate. Alternatively, different intake lines of different delivery pumps can also be connected to the different intake ports 21, leading for example to different injection nozzle elements 11. Also in FIG. 6, for reasons of clarity, no mast housing 43 for the agitator guide mast 40 is shown. It goes without saying that, alternatively but of course, other embodiments without mast housing 43 are also possible, for example to the effect that the agitator service opening 39 can only be closed gas-tightly with a cover, as explained in conjunction with the delivery pump service opening 37.

Figure 7:
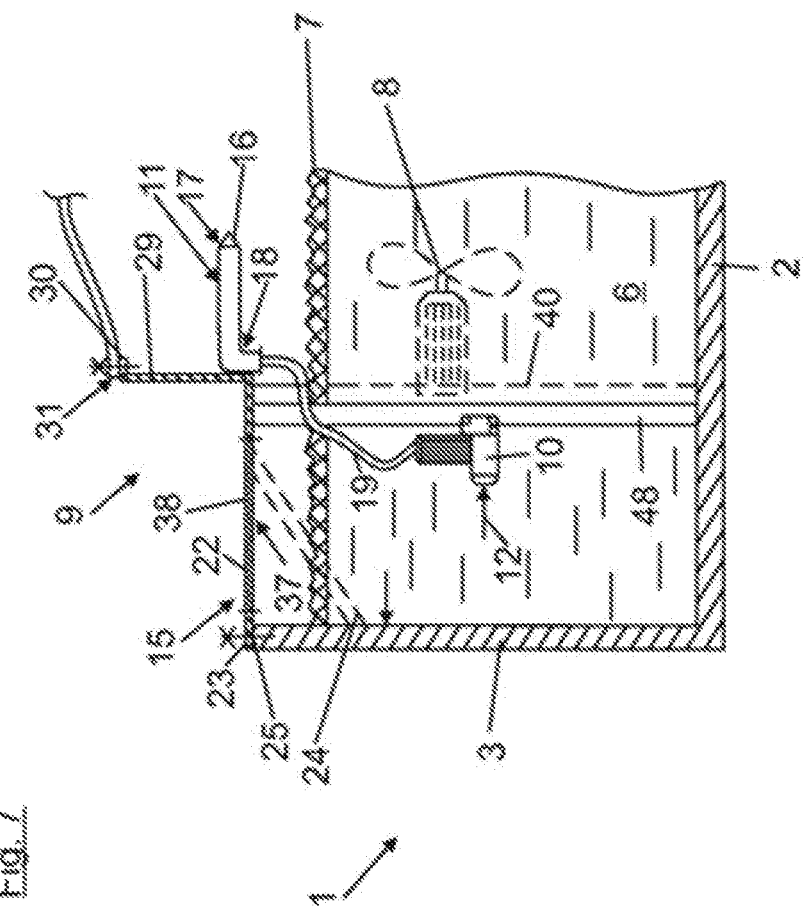
FIG. 7 shows an alternative embodiment to the design according to FIG. 5, with a completely internal delivery pump.

FIG. 7 shows a further alternative embodiment, here only as an example of the design according to FIG. 5, in which the injection nozzle element 11 is fully or completely arranged in the tank inner chamber 5. Here, too, the injection nozzle element 11 is held on the service platform 22 and preferably on the assembly wall 29, for example approximately in the region of the second base side 26. Access to the injection nozzle element can be gained here, for example, via the service opening 37 or, possibly alternatively or additionally, via an inspection opening (not shown here) in the assembly wall 29. The connection-side end 18 of the injection nozzle element 11 located within the fermenter tank 1 is then also connected to a pressure line 19 leading away from the internal delivery pump 10. Such a completely internal arrangement is, of course, also possible in conjunction with other embodiments and arrangements of a pressure line and/or a delivery pump, for example in conjunction with a non-height-adjustable internal delivery pump 10 and/or in conjunction with a rigid pressure pipe as pressure line 19, as shown in the embodiment according to FIGS. 3 and 4. Also in FIG. 7, again for reasons of clarity, no mast housing 43 for the agitator guide mast 40 is shown. It goes without saying that, alternatively but of course, other embodiments without a mast housing 43 are also possible here, for example to the effect that the agitator service opening 39 can only be closed gas-tightly with a cover, as has been explained in conjunction with the delivery pump service opening 37.

The invention claimed is:

1. Biogas plant fermenter tank system comprising:
   a first fermenter tank having an inner chamber adapted to contain a liquid substrate accommodated within said inner chamber;
   at least one stirring apparatus arranged in the tank inner chamber;
   an injection device operatively connected to said first fermenter tank, said injection device having at least one delivery pump for extracting said liquid substrate of said first fermenter tank or from a second fermenter tank;
   said injection device having at least one injection nozzle fluidically connected to the at least one delivery pump for injecting said extracted liquid substrate into said first fermenter tank, wherein the liquid is injected as a liquid jet from above onto a surface of a floating layer of said substrate;
   wherein said stirring apparatus is arranged in the tank inner chamber so that said liquid substrate below said floating layer can be homogenized and/or mixed without stirring said floating layer into said liquid substrate; and
   wherein said fermenter tank includes an opening that is overlaid with a roof, wherein a modular service device is provided which has a service platform arranged adjacent the roof, can be walked on and is formed by a separate component, including a walkable platform plate as a service platform, which is attached by at least one connecting element in a detachable and gastight manner, to a tank side wall, and which includes a roof connection region to which the roof is attached in a detachable and gastight manner, so that said modular service device, including said service platform may be removably attached to and detached from said fermenter tank, as needed; and
   wherein said modular service device further includes at least one injection nozzle attached thereto as a service module injection nozzle.

2. The fermenter tank system set forth in claim 1, wherein said stirring apparatus comprises a plurality of stirring devices spaced apart from one another.

3. The fermenter tank system set forth in claim 1, wherein said stirring apparatus is formed by an agitator, wherein said agitator is slidably attached to a vertically oriented agitator guide mast positioned within said fermenter tank so that said agitator is vertically adjustable therein.

4. The fermenter tank system set forth in claim 1, wherein said at least one injection nozzle projects into the tank inner chamber by a front end, and a rear, connection side end of the injection nozzle is arranged outside the tank inner chamber.

5. The fermenter tank system set forth in claim 4, wherein said at least one injection nozzle is arranged completely in the tank inner chamber.

6. A fermenter tank set forth in claim 4, wherein a pressure line leading away from the delivery pump is connected to the connection-side end of the injection nozzle element located outside or inside the fermenter tank.

7. A fermenter tank set forth in claim 6, wherein an intake side of the delivery pump draws in the liquid substrate accommodated in the fermenter tank.

8. A fermenter tank set forth in claim 7, wherein the pressure line is led from the connection-side end of the injection nozzle located outside the fermenter tank through a pressure line feedthrough of the service platform to an internal delivery pump arranged in the tank inner chamber.

9. A fermenter tank set forth in claim 8, wherein said pressure line is formed by a rigid pressure pipe guided into the fermenter tank, wherein the pressure pipe is supported and/or mounted in the region of the pressure line feedthrough and/or in the tank inner chamber on the tank bottom side, and wherein the internal delivery pump is connected to and/or held on the rigid pressure pipe.

10. A fermenter tank set forth in claim 8, wherein the pressure line, at least a partial region of the pressure line lying in the tank inner chamber, is a pressure line which is variable in shape and/or length including a flexible or telescopic pressure line, and wherein the internal delivery pump is guided height-adjustably along a delivery pump guide mast arranged in the fermenter tank and oriented in the direction of the vertical axis of the tank.

11. A fermenter tank set forth in claim 8, wherein said service platform, directly adjacently to the pressure line feedthrough in the service platform, has a delivery pump service opening which can be closed by a covering device in a gas tight manner for entry and/or access to the internal delivery pump.

12. A fermenter tank set forth in claim 11, wherein the covering device closing the service opening in a gas tight manner is formed by at least one cover and/or by a mast housing which projects upwardly away from the service opening and forms a receiving space for an upper part of the guide mast.

13. A fermenter tank set forth in claim 11, wherein a sealing element is arranged around the service opening, the sealing element, in the sealing position, projects downwardly in the form of a shaft into the tank inner chamber and, at least during maintenance and service works, dips into the liquid substrate which is accommodated in the fermenter tank and is to be fermented, and in a gas tight manner separates a gas phase region, which is annularly enclosed by the sealing element, below the openable service opening, as well as above the substrate from the remaining gas phase region of the tank inner chamber, wherein the sealing element is formed by a rigid, non-displaceable and inflexible collar in the form of a pipe socket which permanently projects from the service opening in the direction of the tank inner chamber.

14. A fermenter tank set forth in claim 6, wherein said pressure line, starting from the connection-side end of the injection nozzle is led to an external delivery pump arranged outside the fermenter tank, the intake side of which has at least one intake line which is led to an intake port in the tank side wall, or through the tank side wall, into the interior of the fermenter tank.

15. A fermenter tank set forth in claim 14, wherein in the tank side wall, as seen in the direction of the vertical axis of the fermenter tank, includes a plurality of intake ports arranged at different heights, in the direction of the vertical axis, are arranged in a row of intake ports lying one above the other and spaced apart from one another, which can be connected to an intake line of the external delivery pump or are connected in valve-controlled fashion.

16. The fermenter tank system set forth in claim 1, wherein said roof is a foil roof.

17. The fermenter tank system set forth in claim 1, wherein said service module injection nozzle is arranged on the service platform on an assembly wall region of the service platform.

18. The fermenter tank system set forth in claim 17, wherein said service platform comprises an assembly wall projecting at an angle from the service platform.

19. The fermenter tank system set forth in claim 18, wherein said service module injection nozzle is guided with its end having the injection nozzle through the assembly wall into the tank inner chamber and is held on the assembly wall.

20. The fermenter tank system set forth in claim 1, wherein said assembly wall projects upwardly from the service platform from an approximately horizontal assembly wall attachment region of said service platform, as viewed in the direction of a vertical axis of the tank, and wherein said assembly wall with its upper edge region lying above the service module injection nozzle in the direction of the vertical axis of the tank forms at least a partial region of the roof connection region at least a partial region of a film roof connection region.

21. The fermenter tank system set forth in claim 20, wherein the service platform, formed by a walkable and/or level platform plate, is designed in the manner of an isosceles trapezium, wherein a first base side adjoins the tank side wall, a second base side is opposite the first base side, and obliquely running leg sides connect the two base sides and said assembly wall extends over the second base side where the assembly wall slopes obliquely downwardly from the second base side towards the first base side.

22. The fermenter tank system set forth in claim 21, wherein the service module injection nozzle element is held and passed through the assembly wall in the region of the second base side.

23. The fermenter tank system set forth in claim 22, wherein said service module injection nozzle is arranged on a tank side wall, as an assembly wall.

24. The fermenter tank system set forth claim 23, wherein the connection side end of the service module injection nozzle is coupled to an adjusting device which can be actuated from outside the fermenter tank and by means of which the position of the service module injection nozzle in the tank inner chamber can be adjusted or changed.

25. The fermenter tank system set forth in claim 24, wherein said service module injection nozzle is attached to the an elastic, tubular intermediate piece and is connected to guide rod of the adjusting device, wherein the guide rod is fixedly attached on an upper side of the service module injection nozzle with respect to the direction of the vertical axis, the guide rod being guided with play or movement and in a gas-tight manner through an assembly wall region to the outside of the fermenter tank, and wherein the guide rod is mounted in a slotted guide which allows the guide rod to be displaced in the direction of the vertical axis and/or transversely to the direction of the vertical axis and/or in the longitudinal direction of the guide rod.

26. A fermenter tank set forth in claim 1, wherein said service platform has an agitator service opening which can be closed by a covering device in a gas tight manner through which opening a stirring device guided height-adjustably on an agitator guide mast is accessible for maintenance and service works and/or can be moved in a gas tight manner out of the fermenter tank and back into the fermenter tank.

* * * * *